United States Patent [19]

Wagner et al.

[11] Patent Number: 5,183,898

[45] Date of Patent: Feb. 2, 1993

[54] PESTICIDAL NITRO-SUBSTITUTED BENZOTHIAZOLONES

[75] Inventors: Klaus Wagner, Cologne; Gerd Hänssler, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 792,850

[22] Filed: Nov. 15, 1991

Related U.S. Application Data

[62] Division of Ser. No. 504,150, Apr. 2, 1990, Pat. No. 5,093,345.

[30] Foreign Application Priority Data

Apr. 7, 1989 [DE] Fed. Rep. of Germany ........ 3911227

[51] Int. Cl.$^5$ ............................................. C07D 277/68
[52] U.S. Cl. .................................................. 548/178
[58] Field of Search .......................................... 548/178

[56] References Cited

U.S. PATENT DOCUMENTS 3,691,186  9/1972  Wagner et al. .................. 548/178

FOREIGN PATENT DOCUMENTS

| 0007161 | 1/1980 | European Pat. Off. |
| 0218972 | 4/1987 | European Pat. Off. |
| 0296146 | 12/1988 | European Pat. Off. |
| 1100372 | 2/1961 | Fed. Rep. of Germany |
| 2101150 | 8/1972 | Fed. Rep. of Germany |
| 2136923 | 2/1973 | Fed. Rep. of Germany |

OTHER PUBLICATIONS

Chemical Abstracts, Band 104, Nr. 5, Feb. 3, 1986, Idemitsu Kosan Co. Ltd. "Benzothiazolones as fungicides" Seite 216, Spalte 2, Zusammenfassung No. 30 422x & Jpn. Kokai Tokkyo Koho JP 60 105 604.
Chemical Abstracts, Band 103, Nr. 19, Nov. 11, 1985, Idemitsu Kosan Co. Ltd. "Benzothiazolinunes" Seite 712, Spalte 2, Zusammenfassung Nr. 160 499t & Japan Kokai Tokkyo Koho JP 60 105 671.
K. Wagner et al., "Uber eine neue Synthese substituierter 2-Benzothiazolone", Chem. Ber. 1974, 107, pp. 306–316.

Primary Examiner—Joseph Paul Brust
Assistant Examiner—MarySusan H. Gabilan
Attorney, Agent, or Firm—Sprung Horn Kramer & Woods

[57] ABSTRACT

Fungicidal nitro-substituted benzothiazolones of the formula

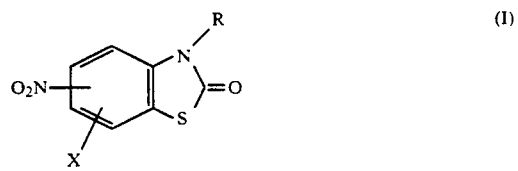

in which
R represents alkyl which is monosubstituted or disubstituted by identical or different substitutents from the group consisting of cyano, carboxyl, alkyl-carbonyl, alkoxycarbonyl, and- alkylaminocarbonyl or and phenyl or phenylcarbonyl in each case optionally monosubstituted to pentasubstituted by identical or different substituents from the group consisting of halogen, alkyl, halogenoalkyl and alkoxy, or R is the radical —CONHR$^1$, in which R$^1$ represents alkyl which is monosubstituted or disubstituted by identical or different substituents from the group consisting of cyano, carboxyl and alkoxycarbonyl, and
X represents hydrogen, halogen, alkyl or halogenoalkyl.

1 Claim, No Drawings

PESTICIDAL NITRO-SUBSTITUTED BENZOTHIAZOLONES

This is a division of application Ser. No. 07/504,150, filed Apr. 2, 1990, now U.S. Pat. No. 5,093,345.

The present invention relates to new nitro-substituted benzothiazolones, to processes for their preparation, to their use in pest-combating agents and to new intermediates.

It has already been disclosed that certain plant diseases can be combated by cyclic sulphur compounds. Thus, for example, 6-methyl-2,3-quinoxalinedithiol cyclocarbonate (quinomethionate/Morestan) can be used against mildew in fruit cultivation (cf. DE-AS (German Published Specification) 1,100,372). However, the action of this known compound is not always satisfactory, in particular at low active compound concentrations.

In addition, nitro- and/or trifluoromethyl-substituted benzothiazolones have been disclosed (cf. Chem. Ber. 107 (1974), 305-315; DE-OS (German Published Specification) 2,101,150), which also have a biological action.

New nitro-substituted benzothiazolones of the general formula (I)

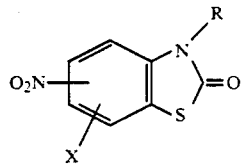

in which

R represents alkyl which is monosubstituted or disubstituted by identical or different substituents from the series comprising cyano, carboxyl, alkylcarbonyl, carbonyl, alkoxycarbonyl and alkylaminocarbonyl or by phenyl or phenylcarbonyl, in each case optionally monosubstituted to pentasubstituted by identical or different substituents from the series comprising halogen, alkyl, halogenoalkyl and alkoxy, or the radical —CONHR$^1$, in which R$^1$ represents alkyl which is monosubstituted or disubstituted in the alkyl moiety by identical or different substituents from the series comprising cyano, carboxyl or alkoxycarbonyl, and X represents hydrogen, halogen, alkyl or halogenoalkyl, have now been found.

In addition, it has been found that the new nitro-substituted benzothiazolones of the general formula (I)

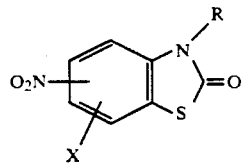

in which

R represents alkyl which is monosubstituted or disubstituted by identical or different substituents from the series comprising cyano, carboxyl, alkylcarbonyl, alkoxycarbonyl and alkylaminocarbonyl or by phenyl or phenylcarbonyl, in each case optionally monosubstituted to pentasubstituted by identical or different substituents from the series comprising halogen, alkyl, halogenoalkyl and alkoxy, or the radical —CONHR$^1$, where R$^1$ represents alkyl which is substituted in the alkyl moiety by cyano, carboxyl or alkoxycarbonyl, and X represents hydrogen, halogen, alkyl or halogenoalkyl, are obtained when (a) nitro-substituted benzothiazolones of the general formula (II)

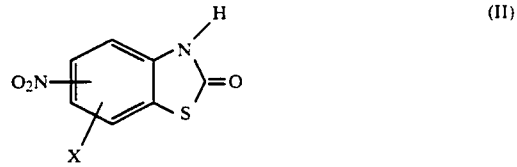

in which

X has the abovementioned meaning, —or alkali metal salts of compounds of the general formula (II)— are reacted with halogen compounds of the general formula (III)

$$X^1-R \quad (III)$$

in which

R has the abovementioned meaning and

X$^1$ represents halogen, if appropriate in the presence of an acid acceptor and if appropriate in the presence of a diluent, or when b) nitro-substituted benzothiazole-3-oxides of the general formula (IV)

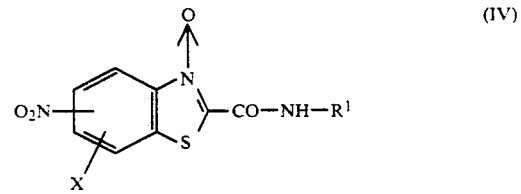

in which

X and R$^1$ have the abovementioned meanings, are reacted with phosphoryl chloride (POCl$_3$), if appropriate in the presence of a diluent.

The new nitro-substituted benzothiazolones of the general formula (I) have interesting biological properties; they are distinguished in particular by a strong fungicidal action.

Surprisingly, the compounds of the formula (I) according to the invention show, for example, a considerably stronger fungicidal action than the known fungicide 6-methyl-2,3-quinoxalinedithiol cyclocarbonate.

Formula (I) provides a general definition of the nitro-substituted benzothiazolones according to the invention. Preferred compounds of the formula (I) are those in which R represents straight-chain or branched alkyl having 1 to 6 carbon atoms, which is monosubstituted or disubstituted by identical or different substituents from the series comprising cyano, carboxyl, C$_1$-C$_4$-alkyl-carbonyl, C$_1$-C$_4$-alkoxy-carbonyl and C$_1$-C$_4$-alkylamino-carbonyl or by phenyl or phenylcarbonyl, in each case optionally monosubstituted to trisubstituted by identical or different substituents from the series comprising halogen, C$_1$-C$_4$-alkyl, C$_1$-C$_4$-halogenoalkyl having 1 to 9 identical or different halogen atoms and C$_1$-C$_4$-alkoxy, or the radical —CONHR$^1$, where R$^1$ represents alkyl having 1 to 6 carbon atoms in the straight-chain or branched alkyl, which is monosubstituted or disubstituted by identical or different substituents from the series comprising cyano, carboxyl or $C_1$-$C_4$-alkoxy-carbonyl, and X represents hydrogen, halogen, $C_1$-$C_4$-alkyl or $C_1$-$C_4$-halogenoalkyl having 1 to 9 identical or different halogen atoms.

Particularly preferred compounds of the formula (I) are those
in which

R represents methyl or ethyl, which is monosubstituted or disubstituted by identical or different substituents from the series comprising cyano, carboxyl, $C_1$-$C_4$-alkyl-carbonyl, $C_1$-$C_4$-alkoxy-carbonyl, or by phenyl or pehnylcarbonyl, in each case monosubstituted to trisubstituted by identical or different substituents from the series comprising fluorine, chlorine, bromine, methyl, ethyl, trifluoromethyl, methoxy and ethoxy, or the radical —CONHR$^1$, in which R$^1$ represents alkyl having 1 or 2 carbon atoms, which is monosubstituted or disubstituted by cyano, carboxyl or $C_1$-$C_4$-alkoxy-carbonyl, and X represents hydrogen, chlorine, methyl or trifluoromethyl.

Halogen represents fluorine, chlorine, bromine or iodine, preferably fluorine, chlorine or bromine, particularly preferably fluorine or chlorine alone or in a combination such as halogenoalkyl, unless otherwise defined.

All radicals which can be substituted are monosubstituted to polysubstituted by identical or different substituents, in particular monosubstituted to pentasubstituted, preferably monosubstituted to trisubstituted and particularly preferably monosubstituted or disubstituted, unless stated otherwise.

If, for example, 6-nitro-benzothiazolone and 4-fluorobenzyl chloride are used as starting substances, the course of the reaction in process (a) according to the invention can be represented by the following equation:

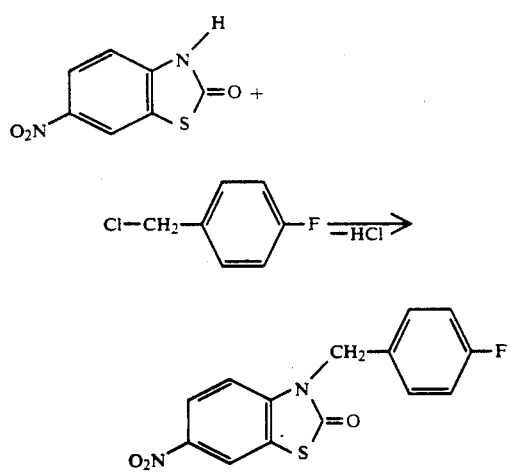

If, for example, 5-methyl-7-nitro-2-cyanomethylaminocarbonyl-benzothiazole-3-oxide and phosphoryl chloride are used as starting substances, the course of the reaction in process (b) according to the invention can be represented by the following equation:

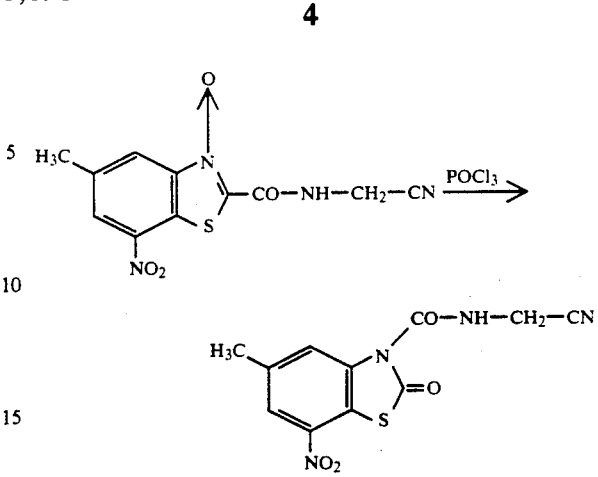

Formula (II) provides a general definition of the nitro-substituted benzothiazolones to be used as starting substances in process (a) according to the invention for the preparation of compounds of the formula (I).

In the formula (II), X preferably or particularly has that meaning which has already been indicated above as preferred or as particularly preferred for X in connection with the description of the compounds of the formula (I) according to the invention.

Examples of the starting substances of the formula (II) which may be mentioned are:

4-nitro-, 5-nitro-, 6-nitro- and 7-nitro-benzothiazolone, 4-chloro-5-nitro-, 4-chloro-6-nitro-, 4-chloro-7-nitro-, 5-chloro-4-nitro-, 5-chloro-6-nitro-, 5-chloro-7-nitro-, 6-chloro-4-nitro-, 6-chloro-5-nitro-, 6-chloro-7-nitro-, 7-chloro-4-nitro-, 7-chloro-5-nitro- and 7-chloro-6-nitro-benzothiazolone, 4-methyl-5-nitro-, 4-methyl-6-nitro-, 4-methyl-7-nitro-, 5-methyl-4-nitro-, 5-methyl-6-nitro-, 5-methyl-7-nitro-, 6-methyl-4-nitro-, 6-methyl-5-nitro-, 6-methyl-7-nitro-, 7-methyl-4-nitro-, 7-methyl-5-nitro- and 7-methyl-6-nitro-benzothiazolone and also 4-trifluoromethyl-5-nitro-, 4-trifluoromethyl-6-nitro-, 4-trifluoromethyl-7-nitro-, 5-trifluoromethyl-4-nitro-, 5-trifluoromethyl-6-nitro-, 5-trifluoromethyl-7-nitro-, 6-trifluoromethyl-4-nitro-, 6-trifluoromethyl-5-nitro-,6-trifluoromethyl-7-nitro-, 7-trifluoromethyl-4-nitro-, 7-trifluoromethyl-5-nitro- and 7-trifluoromethyl-6-nitro-benzothiazolone.

The starting substances of the formula (II) are known and/or can be prepared by processes which are known per se (cf. Chem. Ber. 107 (1974), 305-316; Egypt. J. Chem. 16 (1973), 355-359; DE-OS (German Published Specification) 2,101,150; JP-A 60-105 671; EP-A 218,972).

Formula (III) provides a general definition of the halogen compounds further to be used as starting substances in process (a) according to the invention.

In the formula (III), R preferably or particularly has that meaning which has already been indicated above as preferred or as particularly preferred for R in connection with the description of the compounds of the formula (I) according to the invention and X represents 30 chlorine or bromine.

Examples of the starting substances of the formula (III) which may be mentioned are:

chloroacetone, chloromethyl and bromomethyl tert.-butyl ketone, α-chloro- and β-bromo-acetophenone, chloro- and bromo-acetonitrile and -α- and -β-propionitrile, chloro- and bromo-acetic acid and -α- and -β-propionic acid and their methyl esters, ethyl esters, propyl esters, isopropyl esters, butyl esters and isobutyl esters, chloro- and bromo-malodinitrile, chloro -and bromo-cyanoacetic acid and their methyl esters, ethyl esters, propyl esters, isopropyl esters, butyl esters and isobutyl esters, chloro- and bromo-malonic acid and their di- methyl esters, diethyl ethers, dipropyl esters, diisopropyl, esters, dibutyl esters and diisobutyl esters, 2-chloro-, 3-chloro-, 4-chloro-, 2,4-dichloro-, 2,5-dichloro-, 2,6-dichloro-, 3,4-dichloro- and 3,5-dichlorobenzyl chloride, 2-fluoro-, 3-fluoro-, 4-fluoro-, 2,4-difluoro-, and 3,4-difluoro-benzyl chloride, 2-methyl-, 3-methyl-, 4-methyl- and 3,4-dimethyl-benzyl chloride, 2-trifluoromethyl-, 3-trifluoromethyl- and 4-trifluoromethyl-benzyl chloride and 2-methoxy-, 3-methoxy-, 4-methoxy- and 3,4-dimethoxy-benzyl chloride.

The starting substances of the formula (III) are known chemicals for organic synthesis.

Process (a) for the preparation of the new compounds of the formula (I) is preferably carried out using diluents. Suitable diluents here are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone and also dimethyl sulphoxide, tetramethylene sulphone and hexamethylphosphoramide and in addition also alcohols such as methanol, ethanol, propanol, isopropanol, butanol, isobutanol, sec.-butanol and tert.-butanol.

Acid acceptors which can be employed in process (a) according to the invention are all acid-binding agents customarily utilizable for reactions of this type. Those which are preferred are alkali metals such as, for example, sodium and potassium, alkali metal hydroxides such as, for example, sodium hydroxide and potassium hydroxide, alkaline earth metal hydroxides such as, for example, calcium hydroxide, alkali metal carbonates and alkoxides such as sodium carbonate and potassium carbonate, sodium methoxide and potassium methoxide or sodium ethoxide and potassium ethoxide, and in addition aliphatic, aromatic or heterocyclic amines, for example triethylamine, trimethylamine, dimethylaniline, dimethylbenzylamine, pyridine,1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

The reaction temperatures in process (a) according to the invention can be varied within a relatively wide range. In general, the reaction is carried out at temperatures between 0° C. and 150° C., preferably at temperatures between 10° C. and 120° C.

Process (a) according to the invention is in general carried out under normal pressure. However, it is also possible to work at elevated or reduced pressure.

In order to carry out process (a) according to the invention, the starting substances required in each case are in general employed in approximately equimolar amounts. However, it is also possible to use one of the two components employed in each case in a relatively large excess. The reactions are in general carried out in a suitable diluent and the reaction mixture is stirred for several hours at the temperature required in each case. The work-up in process (a) according to the invention is in each case carried out by customary methods.

Formula (IV) provides a general definition of the nitro-substituted benzothiazole-3-oxides to be used as starting substances in process (b) according to the invention for the preparation of compounds of the formula. (I).

In the formula (IV), X preferably or particularly has that meaning which has already been indicated above as preferred or as particularly preferred for X in connection with the description of the compounds of the formula (I) according to the invention and $R^1$ preferably represents straight-chain or branched alkyl having 1 to 6 carbon atoms, which is substituted by cyano, carboxyl or $C_1$-$C_4$-alkoxy-carbonyl, in particular methyl or ethyl which are substituted by cyano, carboxyl or $C_1$-$C_4$-alkoxy-carbonyl.

Examples of the starting substances of the formula (IV) are shown in Table 1 below.

TABLE 1

Examples of the starting substances of the formula (IV)

$$O_2N-\underset{X}{\underset{|}{\overset{\overset{\displaystyle O}{\uparrow}}{\underset{S}{\overset{N}{\bigcirc}}}}}-CO-NH-R^1 \quad (IV)$$

| Position of $NO_2$ | (Position-)X | $R^1$ |
|---|---|---|
| 6 | — | $-CH_2CH_2CN$ |
| 6 | — | $-CH_2COOCH_3$ |
| 6 | — | $-CH(CH_3)COOC_2H_5$ |
| 6 | — | $-CH_2CH_2COOC_2H_5$ |
| 6 | — | $-CH_2COOH$ |
| 6 | — | $-CH_2COOC_2H_5$ |
| 6 | (7-)Cl | $-CH_2CH_2CN$ |
| 6 | (7-)Cl | $-CH_2COOH$ |
| 6 | (7-)Cl | $-CH_2COOCH_3$ |
| 6 | (7-)Cl | $-CH_2COOC_2H_5$ |
| 6 | (7-)Cl | $-CH_2CH_2COOC_2H_5$ |
| 6 | (7-)Cl | $-CH(CH_3)COOC_2H_5$ |
| 7 | (5-)Cl | $-CH_2CH_2CN$ |
| 7 | (5-)Cl | $-CH_2COOH$ |
| 7 | (5-)Cl | $-CH_2COOCH_3$ |
| 7 | (5-)Cl | $-CH_2COOC_2H_5$ |
| 7 | (5-)Cl | $-CH_2CH_2COOC_2H_5$ |
| 7 | (5-)Cl | $-CH(CH_3)COOC_2H_5$ |
| 7 | (5-)$CF_3$ | $-CH_2CH_2CN$ |
| 7 | (5-)$CF_3$ | $-CH_2COOH$ |
| 7 | (5-)$CF_3$ | $-CH_2COOCH_3$ |
| 7 | (5-)$CF_3$ | $-CH_2COOC_2H_5$ |
| 7 | (5-)$CF_3$ | $-CH_2CH_2COOC_2H_5$ |
| 7 | (5-)$CF_3$ | $-CH(CH_3)COOC_2H_5$ |
| 7 | (5-)$CH_3$ | $-CH_2CH_2CN$ |
| 7 | (5-)$CH_3$ | $-CH_2COOH$ |
| 7 | (5-)$CH_3$ | $-CH_2COOCH_3$ |
| 7 | (5-)$CH_3$ | $-CH_2COOC_2H_5$ |
| 7 | (5-)$CH_3$ | $-CH_2CH_2COOC_2H_5$ |
| 7 | (5-)$CH_3$ | $-CH(CH_3)COOC_2H_5$ |
| 5 | (7-)$CF_3$ | $-CH_2CH_2CN$ |
| 5 | (7-)$CF_3$ | $-CH_2COOH$ |
| 5 | (7-)$CF_3$ | $-CH_2COOCH_3$ |
| 5 | (7-)$CF_3$ | $-CH_2COOC_2H_5$ |
| 5 | (7-)$CF_3$ | $-CH_2CH_2COOC_2H_5$ |
| 5 | (7-)$CF_3$ | $-CH(CH_3)COOC_2H_5$ |
| 5 | (7-)Cl | $-CH_2CH_2CN$ |
| 5 | (7-)Cl | $-CH_2COOH$ |
| 5 | (7-)Cl | $-CH_2COOCH_3$ |
| 5 | (7-)Cl | $-CH_2COOC_2H_5$ |
| 5 | (7-)Cl | $-CH_2CH_2COOC_2H_5$ |

TABLE 1-continued

Examples of the starting substances of the formula (IV)

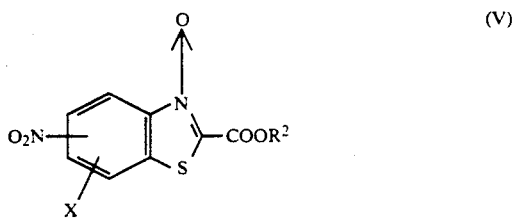

| Position of NO$_2$ | (Position-)X | R$^1$ |
| --- | --- | --- |
| 5 | (7-)Cl | —CH(CH$_3$)COOC$_2$H$_5$ |
| 7 | (5-)Cl | —CH$_2$CH$_2$CN |
| 7 | (5-)Cl | —CH$_2$COOH |
| 7 | (5-)Cl | —CH$_2$COOCH$_3$ |
| 7 | (5-)Cl | —CH$_2$COOC$_2$H$_5$ |
| 7 | (5-)Cl | —CH$_2$CH$_2$COOC$_2$H$_5$ |
| 7 | (5-)Cl | —CH(CH$_3$)COOC$_2$H$_5$ |

The starting substances of the formula (IV) were hitherto unknown from the literature.

The new nitro-substituted benzothiazole-3-oxides of the general formula (IV) are obtained when corresponding 2-alkoxycarbonyl-benzothiazole-3-oxides of the general formula (V)

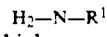

in which

X has the abovementioned meaning and

R$^2$ represents alkyl, preferably having 1 to 4 carbon atoms, are reacted with amines of the general formula (VI)

H$_2$—N—R$^1$      (VI)

in which

R$^1$ has the abovementioned meaning,
if appropriate in the presence of diluents, such as, for example, methanol or ethanol, at temperatures between 0° C. and 100° C.

The 2-alkoxycarbonyl-benzothiazole-3-oxides of the general formula (V) required as intermediates were also hitherto unknown from the literature.

The new 2-alkoxycarbonyl-benzothiazole-3-oxides of the general formual (V) are obtained when corresponding 2-chloro-nitrobenzene derivatives of the general formula (VII)

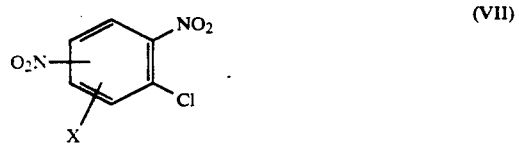

in which

X has the abovementioned meaning, are reacted with mercaptoacetic acid esters of the general formula (VIII)

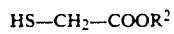      (VIII)

in which

R$^2$ has the abovementioned meaning, in the presence of a base, such as, for example, triethylamine, and in the presence of a diluent, such as, for example, dimethyl sulphoxide, benzene, toluene, tetrahydrofuran, dioxane, methanol, ethanol, propanol, isopropanol and/or water, at temperatures between 0° C. and 100° C., preferably between 20° C. and 80° C.

The starting substances of the formulae (VI), (VII) and (VIII) are known chemicals for organic synthesis.

Process (b) for the preparation of the new compounds of the formula (I) is preferably carried out using diluents. Suitable diluents here are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and n-methylpyrrolidone and also dimethyl sulphoxide, tetramethylene sulphone and hexamethylphosphoramide.

The reaction temperatures can be varied within a relatively wide range in process (b) according to the invention. In general, the reaction is carried out at temperatures between 0° C. and 150° C., preferably at temperatures between 20° C. and 100° C.

Process (b) according to the invention is in general carried out at normal pressure.

In order to carry out process (b) according to the invention, the starting substances required in each case are in general employed in approximately equimolar amounts. However, it is also possible to use one of the two components employed in each case in a relatively large excess. The reactions are in general carried out in a suitable diluent and the reaction mixture is stirred for several hours at the temperature required in each case. The work-up in the process according to the invention is in each case carried out by customary methods.

The active compounds according to the invention have a strong biological action and can be employed practically for combating undesired pests. The active compounds are suitable, for example, for use as plant protection agents, in particular for combating fungi.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum*; Phytophthora species, such as, for example, *Phytophthora infestans*;

Pseudoperonospora species, such as, for example, *Pseudoperonospora humuli* or *Pseudoperonospora cubensis*;

Plasmopara species, such as, for example, *Plasmopara viticola*;

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera,syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The compounds of the formula (I) according to the invention show particularly strong protective action against Pyricularia species, such as, for example, *Pyricularia oryzae,* which cause damage in rice cultivation, and also against Venturia species, such as, for example, *Venturia inaequalis,* which cause damage in fruit cultivation.

A good action is also observed against Plasmopara and Fusarium species.

In some cases, the compounds of the formula (I) according to the invention also show an insecticidal and acaricidal action.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymeth-ylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

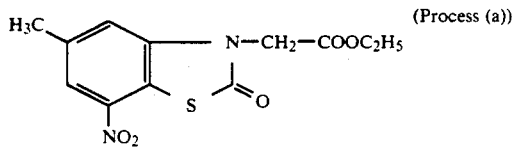
(Process (a))

0.69 g (0.03 g atom) of sodium is dissolved in 150 ml of ethanol. 6.3 g (0.03 mol) of 5-methyl-7-nitrobenzothiazolone are added at room temperature to this solution and 5 g (0.03 mol) of ethyl bromoacetate are then added to the mixture. The reaction mixture is heated under reflux for 8 hours. On cooling, 7.8 g (87% of theory) of 5-methyl-7-nitro-3-ethoxycarbonylmethylbenzothiazolone crystallize out in the form of lemon-yellow needles of melting point 154° C.

Example 2

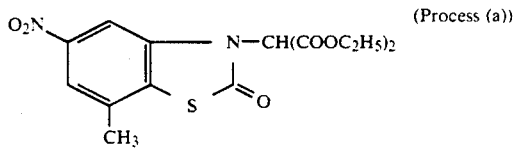
(Process (a))

0.69 g (0.03 g atom) of sodium is dissolved in 100 ml of ethanol. 6.3 g (0.03 mol) of 5-nitro-7-methylbenzothiazolone and then 7.17 g (0.03 mol) of diethyl bromomalonate are added to the solution. The reaction mixture is heated under reflux for 8 hours, poured onto ice and the precipitated product is recrystallized from a little ethanol. 4 g 36% of theory) of 7-methyl-5-nitro-3-(bis-ethoxycarbonyl-methyl)-benzothiazolone are obtained in the form of colorless needles of melting point 97° C.

Example 3

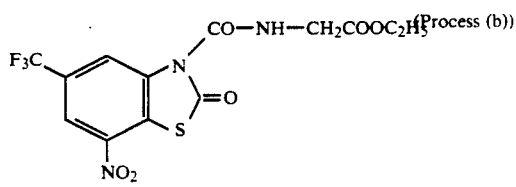
(Process (b))

25 g (0.065 mol) of 2-ethoxycarbonylmethylaminocarbonyl-5-trifluoromethyl-7-nitro-benzothiazole-N-oxide are heated to boiling in 150 ml of chloroform. 11 g (0.075 mol) of phosphorus oxychloride are allowed to drip in at this temperature and the mixture is stirred for 4 hours at 60° C. The 5-trifluoromethyl-7-nitro-benzothia zolone precipitated on cooling the reaction mixture is filtered off and the filtrate is evaporated in vacuo. The residue is recrystallized from ethanol-acetonitrile. 10 g (39% of theory) of 5-trifluoromethyl-7-nitro-3-ethoxy carbonylmethylaminocarbonyl-benzothiazolone are obtained in the form of colorless needles of melting point 150° C.

The compounds of the formula (I) shown in Table 2 below can be prepared analogously to Examples 1 to 3 and corresponding to the general description of the preparation process according to the invention.

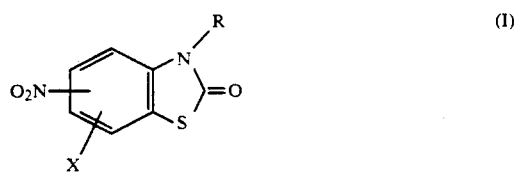

TABLE 2

Examples of the compounds of the formula (I)

| Example No. | Position of NO$_2$ | (Position-)X | R | Melting point (°C.) |
| --- | --- | --- | --- | --- |
| 4 | 5 | (7-)CF$_3$ | —CO—NH—CH$_2$COOC$_2$H$_5$ | 119 |
| 5 | 5 | (7-)CH$_3$ | —CO—NH—CHCOOC$_2$H$_5$<br>\|<br>CH$_3$ | 135 |
| 6 | 7 | (5-)CF$_3$ | —CO—NH—CH$_2$CH$_2$CN | 135 |
| 7 | 7 | (5-)Cl | —CH$_2$COOH | 252 |
| 8 | 7 | (5-)Cl | —CHCOOCH$_3$<br>\|<br>CH$_3$ | 153 |
| 9 | 5 | (7-)CF$_3$ | —CO—NH—CHCOOC$_2$H$_5$<br>\|<br>CH$_3$ | 120 |
| 10 | 7 | (5-)Cl | —CH(COOC$_2$H$_5$)$_2$ | 104 |

TABLE 2-continued

Examples of the compounds of the formula (I)

| Example No. | Position of NO$_2$ | (Position-)X | R | Melting point (°C.) |
|---|---|---|---|---|
| 11 | 7 | (5-)Cl | —CH$_2$—C$_6$H$_4$—Cl (o) | 150 |
| 12 | 7 | (5-)CF$_3$ | —CH(COOC$_2$H$_5$)$_2$ | 90 |
| 13 | 7 | (5-)CF$_3$ | —CH$_2$—CO—CH$_3$ | 202 |
| 14 | 7 | (5-)CF$_3$ | —CH$_2$COOH | |
| 15 | 7 | (5-)CF$_3$ | —CH$_2$—C$_6$H$_4$—Cl (o) | 158 |
| 16 | 7 | (5-)CF$_3$ | —CH$_2$CN | 158 |
| 17 | 7 | (5-)CF$_3$ | —CH$_2$—CO—C(CH$_3$)$_3$ | 158 |
| 18 | 5 | (7-)CF$_3$ | —CH(COOC$_2$H$_5$)$_2$ | 80 |
| 19 | 5 | (7-)CF$_3$ | —CH$_2$—CO—C$_6$H$_5$ | 200 |
| 20 | 5 | (7-)CF$_3$ | —CH$_2$—CO—C(CH$_3$)$_3$ | 178 |
| 21 | 7 | (5-)CH$_3$ | —CH(COOC$_2$H$_5$)$_2$ | 109 |
| 22 | 7 | (5-)CH$_3$ | —CH$_2$—C$_6$H$_4$—Cl (o) | 175 |
| 23 | 6 | (7-)Cl | —CH(COOC$_2$H$_5$)$_2$ | 125 |
| 24 | 7 | (5-)Cl | —CH$_2$—C$_6$H$_4$—F (o) | 136 |
| 25 | 7 | (5-)Cl | —CH$_2$—C$_6$H$_4$—F (m) | 123 |
| 26 | 7 | (5-)Cl | —CH$_2$—C$_6$H$_4$—F (p) | 173 |
| 27 | 6 | — | —CH(COOC$_2$H$_5$)$_2$ | 102 |
| 28 | 5 | (7-)CF$_3$ | —CH$_2$—C$_6$H$_5$ | 129 |
| 29 | 5 | (7-)CF$_3$ | —CH$_2$COOH | 205 |

TABLE 2-continued

Examples of the compounds of the formula (1)

| Example No. | Position of NO$_2$ | (Position-)X | R | Melting point (°C.) |
|---|---|---|---|---|
| 30 | 7 | (5-)CH$_3$ | —CH$_2$—C$_6$H$_4$—F (ortho) | 150 |
| 31 | 7 | (5-)CH$_3$ | —CH$_2$—C$_6$H$_4$—F (meta) | 171 |
| 32 | 7 | (5-)CH$_3$ | —CH$_2$—C$_6$H$_4$—F (para) | 161 |
| 33 | 7 | (5-)CH$_3$ | —CH$_2$—C$_6$H$_4$—OCH$_3$ | 157 |
| 34 | 7 | (5-)CH$_3$ | —CH$_2$—C$_6$H$_4$—Cl (meta) | 187 |
| 35 | 7 | (5-)CH$_3$ | —CH$_2$—C$_6$H$_4$—Cl (para) | 158 |
| 36 | 7 | (5-)CH$_3$ | —CH$_2$—COOH | 250 |
| 37 | 7 | (5-)CH$_3$ | —CH$_2$CN | 199 |

Use Example

The compound shown below was employed as a comparison substance in the following Use Example:

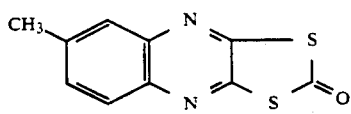

6-Methyl-2,3-quinoxalinedithiol cyclocarbonate (quinomethionate) (cf. DE-AS (German Published Specification) 1,100,372).

Example A

Pyricularia Test (Rice)/Protective

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

A clearly superior action compared to the prior art is shown in this test, for example, by the compounds according to the Preparation Examples (3), (6) and (10).

It is understood that the specification and examples are illustrative but not limitative of the present invention and that other embodiments within the spirit and scope of the invention will suggest themselves to those skilled in the art.

We claim:
1. A nitro-substituted benzothiazole-3-oxide of the formula

17

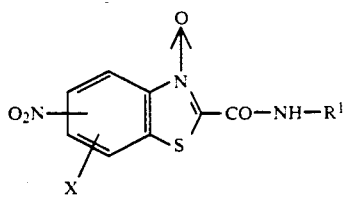

(IV)

in which
X represents hydrogen, halogen, alkyl or halogenoalkyl and
R¹ represents alkyl which is monosubstituted or disubstituted by identical or different substituents from the group consisting of cyano, carboxyl and alkoxycarbonyl.

* * * * *

18

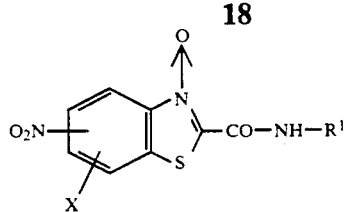

(IV)

in which
X represents hydrogen, halogen, alkyl or halogenoalkyl and
R¹ represents alkyl which is monosubstituted or disubstituted by identical or different substituents from the group consisting of cyano, carboxyl and alkoxycarbonyl.

* * * * *